United States Patent
Cai et al.

(10) Patent No.: US 11,557,382 B2
(45) Date of Patent: Jan. 17, 2023

(54) METHOD FOR AUTOMATICALLY COLLECTING AND MATCHING OF LABORATORY DATA

(71) Applicants: Shenzhen Academy of Inspection and Quarantine, Shenzhen (CN); Shenzhen Customs Information Center, Shenzhen (CN); Shenzhen Customs Animal and Plant Inspection and Quarantine Technology Center, Shenzhen (CN)

(72) Inventors: Yina Cai, Shenzhen (CN); Xianyu Bao, Shenzhen (CN); Lixun Cheng, Shenzhen (CN); Zhouxi Ruan, Shenzhen (CN); Jinxue Peng, Shenzhen (CN); Shaojing Wu, Shenzhen (CN); Yun Guo, Shenzhen (CN); Tikang Lu, Shenzhen (CN); Zhifeng Qin, Shenzhen (CN)

(73) Assignees: SHENZHEN ACADEMY OF INSPECTION AND QUARANTINE, Shenzhen (CN); SHENZHEN CUSTOMS INFORMATION CENTER, Shenzhen (CN); SHENZHEN CUSTOMS ANIMAL AND PLANT INSPECTION AND QUARANTINE TECHNOLOGY CENTER, Shenzhen (CN)

( * ) Notice: Subject to any disclaimer, the term of this patent is extended or adjusted under 35 U.S.C. 154(b) by 172 days.

(21) Appl. No.: 17/102,463

(22) Filed: Nov. 24, 2020

(65) Prior Publication Data
US 2022/0139506 A1    May 5, 2022

(30) Foreign Application Priority Data
Oct. 30, 2020   (CN) .......................... 202011191114.0

(51) Int. Cl.
*G06F 16/22*   (2019.01)
*G06F 16/901*   (2019.01)
(Continued)

(52) U.S. Cl.
CPC ......... *G16H 10/40* (2018.01); *G06F 16/2255* (2019.01); *G06F 16/901* (2019.01); *G06F 16/90344* (2019.01); *G16H 15/00* (2018.01)

(58) Field of Classification Search
CPC .... G16H 10/40; G16H 15/00; G06F 16/2255; G06F 16/901; G06F 16/90344
See application file for complete search history.

(56) References Cited

U.S. PATENT DOCUMENTS

2007/0097755 A1*   5/2007   Marndi ................ G06K 9/0055
                                                        365/189.07
2007/0150469 A1*   6/2007   Simonyi ........... G06F 16/90344
(Continued)

OTHER PUBLICATIONS

Agrawal, Jagrati et al. Efficient pattern matching over event streams. (2008) In Proceedings of the 2008 ACM SIGMOD international conference on Management of data (SIGMOD '08). Association for Computing Machinery, New York, NY, USA, 147-160. https://doi.org/10. (Year: 2008).*

*Primary Examiner* — Tamara T Kyle
*Assistant Examiner* — Lana Alagic

(57) ABSTRACT

The present disclosure provides a method for automatically collecting and matching laboratory data, including: obtaining a creation time of experimental data, determining target experimental data corresponding to a target time in accordance with the creation time, segmenting the target experimental data into a plurality data blocks, generating a data block index table, including at least one data block identifier, according to the data blocks, selecting a target matching mode from a plurality of predetermined matching modes according to the data block index table, obtaining the data (Continued)

block identifier upon determining the target experimental data in a storage node is loaded, and extracting data content in the target experimental data corresponding to the data block identifier by the target matching mode. This method may greatly reduce the number of string matching and may reduce the complexity of the algorithm.

10 Claims, 4 Drawing Sheets

(51) Int. Cl.
*G06F 16/903* (2019.01)
*G16H 10/40* (2018.01)
*G16H 15/00* (2018.01)

(56) References Cited

U.S. PATENT DOCUMENTS

| | | | |
|---|---|---|---|
| 2010/0042790 A1* | 2/2010 | Mondal | G06F 3/0689 709/215 |
| 2010/0266215 A1* | 10/2010 | Hua | G06K 9/62 382/229 |
| 2012/0130983 A1* | 5/2012 | Ryan | G06F 16/90344 707/715 |
| 2013/0138620 A1* | 5/2013 | Yakushev | G06F 16/951 707/698 |

\* cited by examiner

METHOD FOR AUTOMATICALLY COLLECTING AND MATCHING OF LABORATORY DATA

CROSS REFERENCE TO RELATED APPLICATIONS

The present disclosure claims priority to Chinese Patent Application No. CN 202011191114.0, filed Oct. 30, 2020, which is hereby incorporated by reference herein as if set forth in its entirety.

BACKGROUND

1. Technical Field

The present disclosure relates to data processing field, and particularly to a method for automatically collecting and matching laboratory data.

2. Description of Related Art

With the refinement of laboratory testing technology, how to extract useful information from a large amount of data has become the key of research on data processing in experimental data files. String matching is mainly used for data collection in the text domain. After decades of development, string pattern matching is widely used in computer, sensitive word detection, biology, text processing, statistics and other fields.

Nowadays, customs laboratories have a wide variety of testing equipment, various factory sources, and business volume increasing year by year. There are still manual recruitment data, which leads to prominent problems such as long detection cycles and high incidental errors. It is difficult to meet the large business volume and the error-free requirement of data processing of customs laboratories. Among them, string matching algorithm is an important field of data processing research. Having an efficient string matching algorithm can significantly shorten the detection cycle, which is an important factor to reduce error rate of automatic collection. However, because the experimental data file issued by the laboratory testing equipment has a fixed format and only a few sets of data need to be matched in a large experimental data file, the current string matching algorithm can be used to match the string of the experimental data file, but often the calculation is too complex, the matching efficiency is low, occupying a great amount of the system memory. Moreover, there is a certain error rate in practical use, which is difficult to meet the current requirement of customs laboratory.

Therefore, in order to improve the speed of string matching in experimental data files, to reduce the maximum memory usage, and to shorten the inspection time of samples in customs laboratories, on the prerequisite of ensuring the accuracy of data matching, to achieve effective management, solving string matching in experimental data files has become a critical issue.

DETAILED DESCRIPTION

In order to make the objects, features and advantages of the present disclosure more obvious and easy to understand, the technical solutions of the present disclosure will be further described below with reference to the drawings and the embodiments. Apparently, the described embodiments are part of the embodiments of the present disclosure, not all of the embodiments. All other embodiments obtained by those skilled in the art based on the embodiments of the present disclosure without creative efforts are within the scope of the present disclosure.

It should be noted that string matching means that when given a specific set of string group Pn, for any text string T with a length of m, the length of Pn is required to be less than m, to find all of the locations where the Pn appear in the text string T. When there are multiple matching modes, the matching modes can be divided into two types according to the number of pattern strings: single-pattern matching and multi-pattern matching. The simplest way to perform multi-pattern matching is to perform single-pattern matching for multiple times.

At the beginning of the period string matching research, the moving distance of the pattern string or text string in the matching process was increased according to the characteristics of the prefix and suffix of the regular pattern string itself. Later, the AC optimization algorithm was proposed to improve the Trie tree and to construct the SHIFT table with respective lengths to optimize the WM method and skipping process, and a subset confirmation mechanism of the WM algorithm was designed to improve the matching speed.

However, these string matching modes all apply one parameter to all files. it is inevitable that there will be problems such as low matching speed, long preprocessing time and large memory usage, which are not suitable for data processing in customs laboratories.

Figure 1:
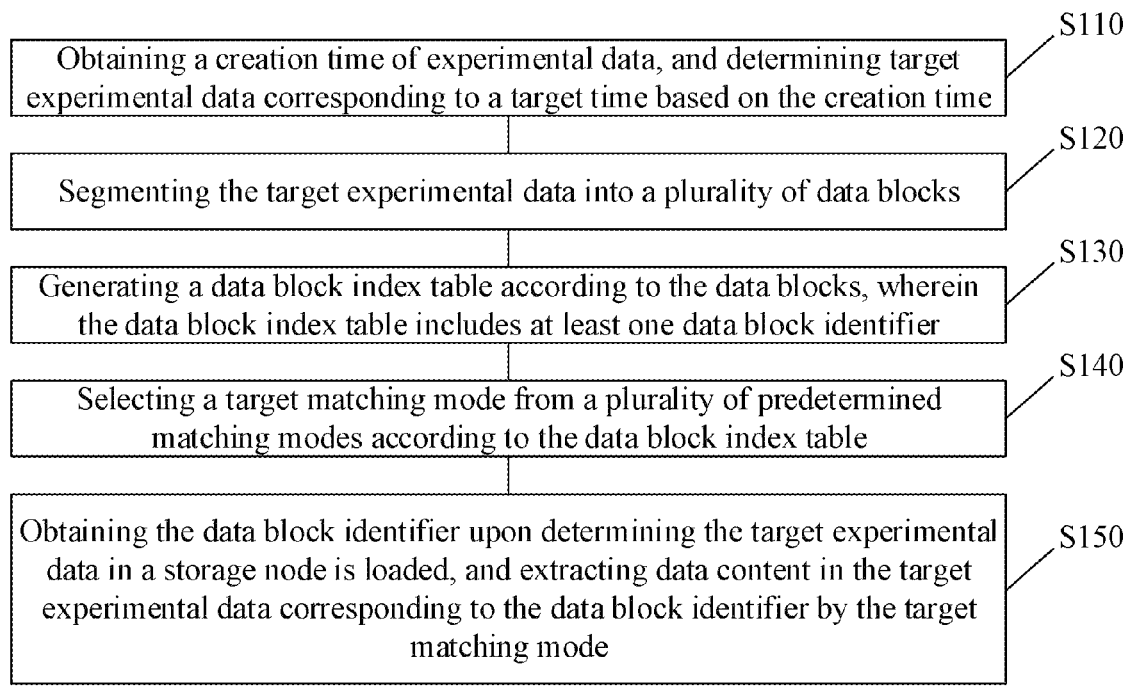
FIG. 1 is a flow chart of an embodiment of a method for automatically collecting and matching laboratory data in the present disclosure.
Figure 2:
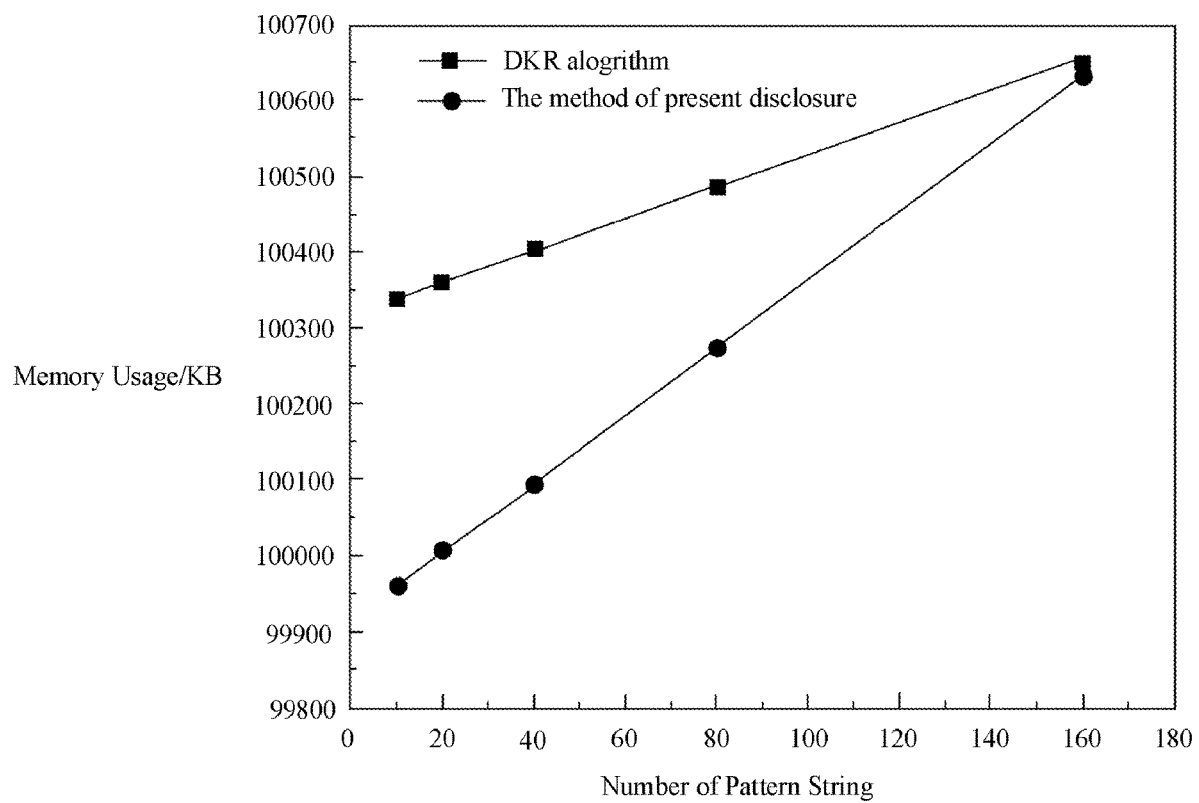
FIG. 2 is a logistics chain network of an embodiment of a method for automatically collecting and matching laboratory data in the present disclosure.

Referring to FIG. 1, FIG. 1 illustrates a method for automatically collecting and matching laboratory data of an embodiment of the present disclosure. The method includes the following steps.

S110: obtaining a creation time of experimental data, and determining target experimental data corresponding to a target time in accordance with the creation time.

S120: segmenting the target experimental data into a plurality of data blocks.

S130: generating a data block index table according to the data blocks, wherein the data block index table includes at least one data block identifier.

S140: selecting a target matching mode from a plurality of predetermined matching modes according to the data block index table.

S150: obtaining the data block identifier upon determining the target experimental data in a storage node is loaded, and extracting data content in the target experimental data corresponding to the data block identifier by the target matching mode.

In one embodiment of the present disclosure, the method for automatically collecting and matching laboratory data has high adaptability and can be applied to most testing equipment. It may greatly reduce the number of string matching and may reduce the complexity of the algorithm. Moreover, it may increase the string matching speed and has better performance while reducing the memory usage.

In one embodiment of the present disclosure, the method for automatically collecting and matching laboratory data will be further explained below.

As described above, S110 is to obtain a creation time of experimental data, and determining target experimental data corresponding to a target time in accordance with the creation time.

It should be noted that, because the experimental data files are processing within one day, time is used as the barrier factor. The creation time of the experimental data is compared with the environmental time of the processing system when the method of the present disclosure is executed, so as to preliminarily filter out the experimental data that is not generated by today.

In one embodiment, the method further includes the step of obtaining the granularity parameter of the target experimental data, and generating a target hash value corresponding to the target experimental data according to the granularity parameter.

It should be noted that the Whole File Detection (WFD) technology may be used to calculate the hash value of the experimental data based on the granularity parameter of the file corresponding to the experimental data, so as to not to load the duplicated files and to filter out the files that have been read.

In one embodiment, the method further includes the step of storing the target hash value in a target storage node upon determined the target hash value is different from a hash value stored in the target storage node.

In one embodiment, the processes of capturing the experimental data may include the following steps.

a. Storing the experimental data file in a storage node A (the target storage node).

b. recording current system time after all files are stored, wherein the system time is the actual time of the current storage environment, and the unit of the recorded time is accurate to day.

c. conducting broad-prioritize traverse via a queue structure, wherein the file is printed and removed from the head at first, and then add the sub-files under the file to the queue, so that the file level is the same when traversing, so as to achieve breadth-prioritize traverse of the file and to obtain the files.

d. extracting a creation time of a current file information object via a file object corresponding to a specified path file, and converting a time format into year-month-day format.

e. determining whether the experimental data file is detected today by comparing the creation time, having the attributes of year-month-day, with the system time, having the attributes of year-month-day. If the time is the same, it indicates that the experimental data file is detected by today, and the hash value of the file is further calculated. If the time is different, it indicates that the file is not the experimental data file today.

The whole file is an granular. Instead of dividing the file, the hash value of the entire file is calculated via using the Message-Digest Algorithm 5 (MD5) or the Secure Hash Algorithm 2 (SHA-2).

The calculated hash value is compared with the stored hash value to determine whether there is any duplication. The stored hash value refers to the stored hash value of the file that every time when the file is read. If the hash value is duplicated, it indicates that the file has been read before or the file is duplicated. If the hash value is not duplicated, the content of the file is read and the hash value corresponding to the file may be stored.

The experimental data files not detected by today, the duplicated files and the files that have been read before are moved to a storage node B by a file transferring method so as to facilitate to load the new experimental data files stored in the storage node A in the future.

As the number of captured experimental data file increases, the amount of the stored hash value increases, which may cause the calculation time of comparing the hash value of the file with the stored hash value increase. Therefore, the stored hash value shall be cleaned up regularly while cleaning up the experimental data in the storage node B.

In the file capture process of the method of present disclosure, two barrier factors, the file creation time for preliminarily screening and the file hash value for fine screening, are established. During the preliminarily screening, all non-today experimental data may be filtered with the advantages of low calculation requirements and low calculation volume. In the file screening, by calculating the overall hash value of the file to filter the experimental data that has been read today. Therefore, the method has advantages of wide application range and high accuracy.

As described above, S120 is to segment the target experimental data into a plurality of data blocks.

In one embodiment of the present disclosure, the specific process of segmenting the target experimental data into a plurality of data blocks is further described in the following description.

It should be noted that the Content-Defined Chunking (CDC) algorithm is a segmenting strategy that uses Rabin fingerprints to segment files into chunks of different sizes. That is, the CDC algorithm uses a fixed-size data segmentation window to divide the file. When a Rabin fingerprint identifier of the data segmentation window matches an expected fingerprint identifier, locating a segmentation point at the current position. The process is repeated until the entire file is segmented, so that the entire file may be segment into a plurality of data blocks according to the segmentation point.

The step of determining a fingerprint identifier of a data segment corresponding to the target experimental data selected by the data segmentation window of a predetermined size is further described in the following description.

It should be noted that since the current CDC algorithms of string matching mainly adopt a fixed-size data segmentation window, thus it has great limitations. Therefore, the method of the present disclosure adopts a data block segmenting method suitable for the fixed file format based the fixed file format in the original record file of the experiment issued by the testing equipment, so as to overcome the current technical defects.

In on embodiment of the present disclosure, the step of determining a fingerprint identifier of a data segment corresponding to the target experimental data selected by the data segmentation window of a predetermined size is further described in the following description.

The step of determining a byte size of the data segment corresponding to the target experimental data in the data segmentation window is further described below.

When the byte size is within a predetermined range, the fingerprint identifier is generated according to the data segment. When the byte size is not within the predetermined range, the data segmentation window is moved by a sliding unit along a predetermined direction.

In one embodiment of the present disclosure, the sliding unit may be defined by the height of the row having the highest frequency, and a gap between the rows of the target experimental data.

The step of determining a data segmentation point of the target experimental data according to a position of a data segment and the fingerprint identifier is further described below.

In on embodiment of the present disclosure, the step of determining a data segmentation point of the target experimental data according to a position of a data segment and the fingerprint identifier is further described later.

The step of determining an expected fingerprint identifier from a predetermined expected fingerprint identifier sequential table according to the position of the data segment is further described below.

When the fingerprint identifier matches the expected fingerprint identifier, a lower boundary of the current data segmentation window is determined as the data segmentation point. When the fingerprint identifier does not match the expected fingerprint identifier, the data segmentation window is moved by one sliding unit along the predetermined direction.

In on embodiment, the step of determining an expected fingerprint identifier from a predetermined expected fingerprint identifier sequential table according to the position of the data segment is further described in the following description.

Determining a partitioning number of the current data block segmentation according to the position of the data segment; determining the expected fingerprint identifier from the expected fingerprint identifier sequential table according to the partitioning number.

It should be noted that the sequential table is composed of the partitioning number, the predetermined expected fingerprint identifier and a corresponding data block identifier. That is, when the fingerprint identifier matches the expected fingerprint identifier, the lower boundary of the current data segmentation window is determined as the data segmentation point, and the data block identifier is recorded.

The expected fingerprint identifier may be a fingerprint indication scope corresponding to the size of the data block set by the user according to his own search habits, or may be a fingerprint indication scope obtained by pre-learning or pre-training through existing artificial intelligence algorithms or artificial intelligence-like algorithms.

The step of segmenting the target experimental data into corresponding data blocks in accordance with the data segmentation point is further described below.

In one embodiment of the present disclosure, the date segmentation process is described below.

Loading the captured experimental data file; setting the size of the data segmentation window from the beginning of the experimental data file, using the height of the row having the highest frequency, and a gap between the rows as a sliding unit to slide until the data segmentation window of the predetermined size is full loaded.

Because the original experimental record file formats issued by same the testing equipment is consistent, the position of the desired boundary may be determined by pre-learning to set the size of bytes of the data segmentation window. After the data segmentation window is fully loaded with data, determining whether the byte size of the data segmentation window is within the set range. If the byte size of the data segmentation window is within the set range, calculating the Rabin fingerprint identifier of the data of the data segmentation window. If the byte size of the data segmentation window is not within the set range, the data segmentation window slides down by one slide unit.

The Rabin fingerprint identifier of the data of the data segmentation window is compared with the sequential table of the expected fingerprint identifier of the predetermining data segmentation window.

For example, the first expected fingerprint identifier of the sequential table is "A", and the Rabin fingerprint identifier of a certain position "D" of the data segmentation window is "f." When fmodD=A at a certain position of the data segmentation window, the lower boundary of the data segmentation window is determined as a segmenting line to segment the text and to create a block. If fmodD≠A, the data segmentation window slides down by one sliding unit, and the Rabin fingerprint identifier of the data segmentation window is recalculate, and the recalculated result is compared with the expected fingerprint identifier.

Determining whether the data segmentation window has reached the end of the file, that is, to determine whether the file has been entirely segmented. If the file hasn't been entirely segmented, the data segmentation window slides down by one sliding unit. If the file has been entirely segmented, the file segmentation process is completed.

In the application of string matching, the method of the present disclosure sets the expected fingerprint identifier based on the position of the text string which matches the pattern string, so that the pattern string may complete the string matching in the front part of the data block when the pattern string and the data block are matching the string. The matching process the rest of the unmatched text stops when matching is completed, so that it may improve the matching speed the CDC technology and also keep correctness of the matching process.

Comparing with the traditional CDC algorithm, the method of the present disclosure has the following improvements: ① the height of the row having the highest frequency, and a gap between the rows is set as the sliding unit for the downward movement of the data segmentation window, ② the range of the byte size of the data segmentation window is set to preliminarily filter out most of the data segmentation window positions that do not meet the segmentation conditions, ③ the sequential table of the expected fingerprint identifier of the data segmentation window is formulated to make the data block size of the file segmentation more accurately. With this improvement, comparing with the traditional CDC block segmentation algorithm, the method of the present disclosure has better good performance, and may reduce the complexity of the file block segmentation process, and may improve the block segmentation efficiency of the original experimental record file.

As described above, S130 is to generate a data block index table, including a data block identifier, according to the data blocks.

In one embodiment of the present disclosure, the step of generate a data block index table according to the data blocks is described below.

The step of determining the hash value, the pattern string and a bit-address corresponding to the data block is further described below.

The data block index table is generated according to the data block identifier, the hash value, the pattern string and the bit-address.

As described above, S140 is to determine a target matching mode from a plurality of predetermined matching modes according to the data block index table.

In one embodiment of the present disclosure, the step of determining a target matching mode from a plurality of predetermined matching modes according to the data block index table is described below.

The step of determining the mapping between the pattern string and the data block according to the data block index table is further described below.

According to the mapping, the shortest time-consuming matching mode is selected as the target matching mode from the predetermined matching modes.

It should be noted that because of the characteristic of the large text string T and the small amount of the pattern strings Pn of the original experimental record file of the customs laboratories, adopting the traditional string matching mode may have problems such as spending more pattern string matching times, costing longer matching time and causing higher computational complexity. Therefore, the method of the present disclosure proposes an optimized string matching algorithm based on data index. After the file is segmented into blocks, the Cyclic Redundancy Check (CRC) 32 algorithm, the MD5 hash algorithm, or SHA-2 hash algorithm may be used to calculate the hash value, the pattern string and the bit address of the data block to form the data block index table. Then, the pattern string Pn may be quickly matched to the corresponding data block through the data block index table. Finally, the pattern string may use the simplest single-pattern matching Brute Force (BF) algorithm to perform the string matching regarding the mapped data block to obtain the string matching result. The data block index table in the string matching optimization algorithm based on data block index is shown in Table 1.

TABLE 1

| Data Block Identifier | Hash Value | Pattern String | Bit-Address |
|---|---|---|---|
| Chunk-1 | Chunk1-Hash | $P_1$ | 1-H |
| Chunk-2 | Chunk2-Hash | $P_2$ | 2-H |
| ... | ... | ... | ... |
| Chunk-n | Chunk3-Hash | $P_n$ | N-H |

It can be seen from Table 1 that each record of the data block index table uses the data block identifier as the primary key. At the same time, the table also stores the hash value of the data block, the corresponding pattern string and the bit-address. The bit-address represents the actual physical location of the data. In the data block index table, the records are stored in an organized manner according to the data block identifier to ensure the searching efficiency and improve the matching efficiency of the algorithm.

The precise matching algorithm between the pattern string and the data block may be selected a suitable single-pattern matching algorithm according to the length of the pattern string, thereby improving the matching efficiency. When the text position of the pattern string matching is relatively concentrated, the text may be segmented into a data block, and the single pattern matching algorithm may be converted into the AC algorithm, the sunny algorithm or the Wu-Manber (WM) algorithm to perform the precise matching between the pattern string and the data block, thereby reducing the number of blocks and avoiding the blocks to be too little. According to the corresponding mapping between the pattern string and the data block, a better matching algorithm may be selected, thereby constructing a flexible pattern string matching algorithm. This algorithm not only improves the efficiency of the string matching, but also has a high adaptability, which may be apply to different experimental original record files.

As described above, the step S150 is to obtain the data block identifier upon determining the target experimental data in a storage node is loaded, and extract data content in the target experimental data corresponding to the data block identifier by the target matching mode.

In one embodiment of the present disclosure, the relevant information of the experiment environment is shown in Table 2. The memory usage and the method of the matching speed experiment are introduced to test the method of the present disclosure. The instruments used in the experiment and the original record files of the experiment are provided by Shenzhen Customs Laboratory. The unit of experiment running time is mini-second (ms).

TABLE 2

| Hardware Environment | System | Ubuntu 16.04 (64 gigabite) |
|---|---|---|
| | Memory | Intel ® Core ™ 17-2670QM CPU@2.20 GHz |
| | Core Number | 4 |
| Software Environment | Programming Language | C |
| | Programmer | gcc version 5.4.0 |

This experiment compares the memory usage of the method of the present disclosure and the DKR algorithm under the same experimental conditions. The experiment selects the original experimental record file issued by the Agilent liquid chromatograph 1290Q (D030202), and the number of pattern strings are 10, 20, 40, 80 and 160 respectively. The length of the pattern string is between 2 to 10. The memory usage adopts the size of the largest resident set to represent the memory usage during program operation. The memory usage of the algorithm is shown in FIG. 3

Figure 3:
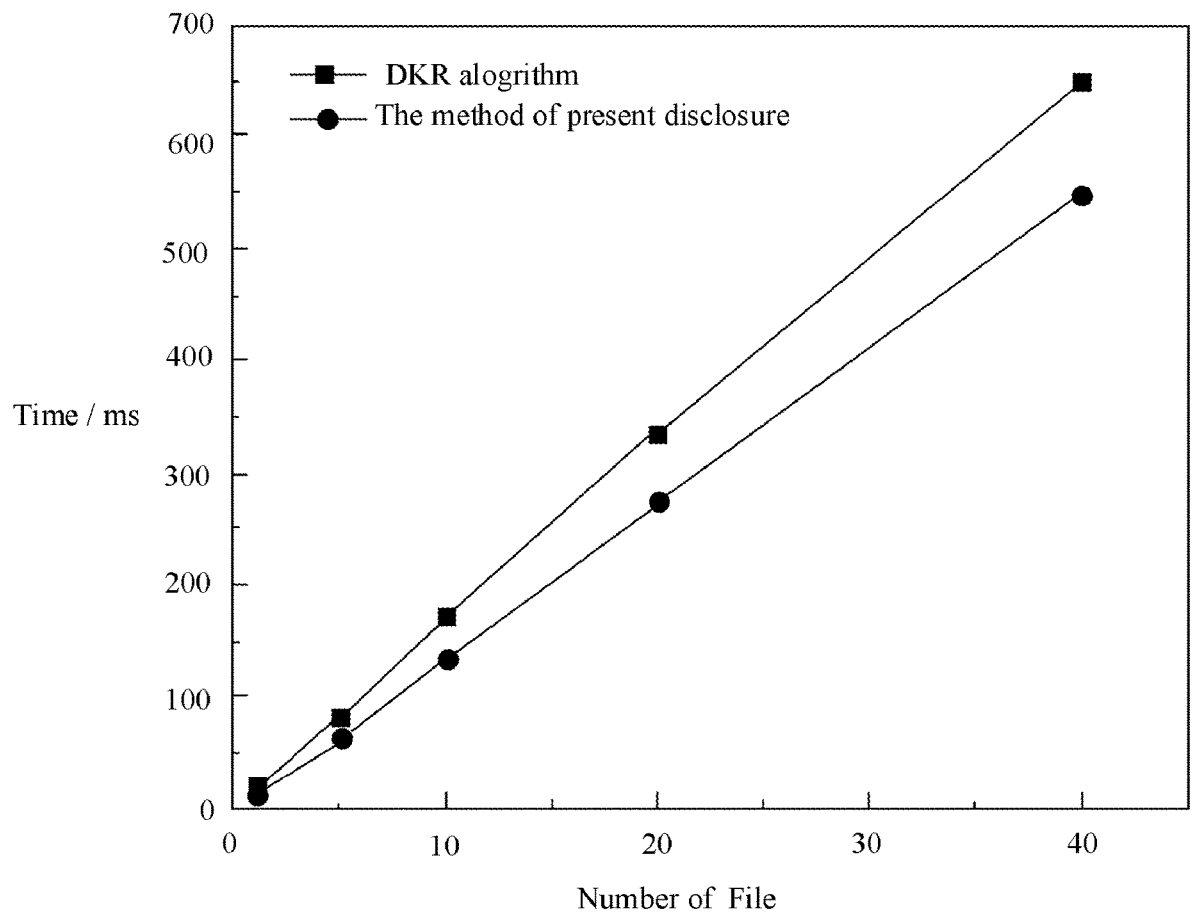
FIG. 3 is a schematic diagram of a first sub-chain network of an embodiment of a method for automatically collecting and matching laboratory data in the present disclosure.

It can be seen from FIG. 3, comparing with the DKR algorithm, the method of the present disclosure has better performance in terms of memory usage regarding the original laboratory record file matching with the pattern strings less than 10. However, as the number of the pattern string increases, the advantage of DKR algorithm in memory usage becomes more obvious, and it becomes more popular when the matching pattern string is at a large scale.

Another experiment compares the matching speed of the method of the present disclosure and the DKR algorithm under the same conditions. Eight sets of tests are conducted in total according to the number of original experimental records, and the original experimental records are randomly selected to be 1, 5, 10, 20 and 40 respectively. In order to avoid abnormal results due to coincident, each test is matched for ten times, and the average matching time is calculated. The final comparison result is shown in FIG. 4.

Figure 4:
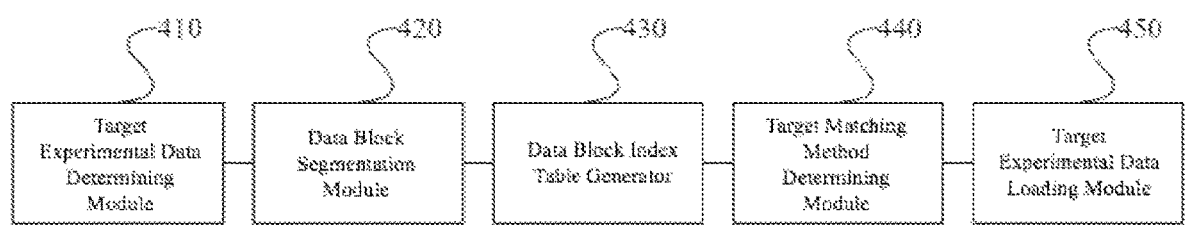
FIG. 4 is a block diagram of an embodiment of a device for automatically collecting and matching laboratory data in the present disclosure.

It can be seen from FIG. 4 that the matching time of the method of the present disclosure is significantly higher than that of the DKR algorithm. When the original experimental record reaches ten copies, the method of the present disclosure only needs 121.7 ms, that is, the matching speed is 12.17 ms per copy. The matching time of the DKR algorithm is 172.4 ms, that is, the matching speed is 17.24 ms per copy. It can be seen that the matching speed of the method of the present disclosure is 29.41% faster than that of the DKR algorithm. It shows that the method of the present disclosure may achieve a better result.

Regarding the device embodiment, it is basically similar to the method embodiment, the description is relatively simple, and for related parts, please refer to the description of the method embodiment.

Referring to FIG. 4, FIG. 4 illustrates a block diagram of an embodiment of a device for automatically collecting and matching laboratory data in the present disclosure. The device includes a target experimental data determining module 410, a data block segmentation module 420, a data block index table generator 430, a target matching mode determining module 440 and a target experimental data loading module 450.

The target experimental data determining module 410 is configured to obtain the creation time of the experimental data and to determine the target experimental data corresponding to the target time according to the creation time.

The data block segmentation module 420 is configured to segment the target experimental data into a plurality of data blocks.

The data block index table generator 430 is configured to generate the data block index table according to the data blocks, wherein the data block index table includes a data block identifier.

The target matching mode determining module 440 is configured to determine the target matching mode from a plurality of predetermined matching modes according to the data block index table.

The target experimental data loading module 450 is configured to load the target experimental data from the storage node according to the target matching mode.

In one embodiment of the present disclosure, the device of the present disclosure further include a target hash value generator and a target hash value storage module. The target hash value generator is configured to obtain the granularity parameter of the target experimental data and generate the target hash value corresponding to the target experimental data according to the granularity parameter. The target hash value storage module is configured to store the target hash value in the target storage node upon determined the target hash value is different from the hash value stored the target storage node.

In one embodiment of the present disclosure, the data block segmentation module 420 further includes a fingerprint identifier determination sub-module, a data segmentation point determination sub-module and a data block segmentation sub-module.

The fingerprint identifier determination sub-module is configured to determine the fingerprint identifier of the data segment corresponding to the target experimental data selected by the data segmentation window of the predetermined size.

The data segmentation point determination sub-module is configured to determine the data segmentation point of the target experimental data according to the position of the data segment and the fingerprint identifier.

The data block segmentation sub-module is configured to segment the target experimental data into corresponding data blocks in accordance with the data segmentation point.

In one embodiment of the present disclosure, the fingerprint identifier determination module further includes a byte size determining sub-module, a fingerprint identifier generating sub-module and a first data segmentation window moving sub-module.

The byte size determining submodule is configured to determine the byte size of the data segment corresponding to the target experimental data in the data segmentation window.

The fingerprint identifier generating sub-module is configured to generate the fingerprint identifier according to the data segment when the byte size is within the predetermined range.

The first data segmentation window moving sub-module is configured to move the data segmentation window by one sliding unit along the predetermined direction when the byte size is not within the predetermined range.

In one embodiment of the present disclosure, the data segmentation point determination sub-module further includes a data segmentation point determination sub-module based on the lower boundary and a second data segmentation window moving sub-module.

The data segmentation point determination sub-module based on the lower boundary is configured to determine the lower boundary in the current data segmentation window as the data segmentation point when the fingerprint identifier matches the expected fingerprint identifier.

The second data segmentation window moving sub-module is configured to move the data segmentation window by one sliding unit along the predetermined direction when the fingerprint identifier does not match the expected fingerprint identifier.

In one embodiment of the present disclosure, the device further includes a sliding unit determination module configured to determine the sliding unit according to the height of the row having the highest frequency, and a gap between the rows in the target experimental data.

In one embodiment of the present disclosure, the device further includes an expected fingerprint identifier sequential table determination module configured to determine the expected fingerprint identifier sequential table according to the parameters of the data segmentation window, wherein the expected fingerprint identifier sequential table includes all the expected fingerprint identifiers corresponding to the data segmentation window.

In one embodiment of the present disclosure, the data block index table generator 430 further includes a data block parameter determination sub-module and a data block index table generating sub-module.

The data block parameter determination sub-module is configured to determine the hash value, the pattern string and the bit-address corresponding to the data block.

The data block index table generating sub-module is configured to generate the data block index table according to the data block identifier, the hash value, the pattern string and the bit-address.

In one embodiment of the present disclosure, the target matching mode determination module 440 further includes a mapping determining sub-module and a target matching mode selecting sub-module.

The mapping determining sub-module is configured to determine the mapping between the pattern string and the data block according to the data block index table.

The target matching mode selecting sub-module is configured to select the matching mode having the shortest time-consuming from the predetermined matching modes according to the mapping as the target matching mode.

The above is a detailed description of method for automatically collecting and matching laboratory data provided in this disclosure. The descriptions of the forgoing embodiment are only used to help understand the technical schemes of the present disclosure and their core ideas. At the same time, for those skilled in the art, according to the ideas of the present disclosure, there will be changes in the specific implementation and the application scope. In summary, the contents of the present disclosure should not be construed as limitations to the present disclosure.

What is claimed is:

1. A method for automatically collecting and matching laboratory data, wherein the method comprises steps of:

obtaining a creation time of experimental data input from at least one testing equipment, and determining target experimental data corresponding to a target time in accordance with the creation time;

segmenting the target experimental data into a plurality of data blocks;

generating a data block index table according to the data blocks, wherein the data block index table comprises at least one data block identifier;

selecting a target matching mode from a plurality of predetermined matching in modes according to the data block index table;

obtaining the data block identifier upon determining the target experimental data in a storage node is loaded, and extracting data content in the target experimental data corresponding to the data block identifier by the target matching mode;

wherein the method further comprises:
obtaining a granularity parameter of the target experimental data;
generating a target hash value corresponding to the target experimental data according to the granularity parameter; and
storing the target hash value in a target storage node upon determining the target hash value is different from a hash value stored in the target storage node;

wherein the segmenting step further comprises:
determining a fingerprint identifier of a data segment corresponding to the target experimental data selected by a data segmentation window of a predetermined size;
determining a data segmentation point of the target experimental data according to a position of a data segment and the fingerprint identifier; and
segmenting the target experimental data into corresponding data blocks in accordance with the data segmentation point;

wherein the step of determining a data segmentation point of the target experimental data according to a position of a data segment and the fingerprint identifier further comprises:
determining an expected fingerprint identifier from a predetermined expected fingerprint identifier sequential table according to the position of the data segment;
configuring a lower boundary of the current data segmentation window as the data segmentation point when the fingerprint identifier matches the expected fingerprint identifier; and
moving the data segmentation window by one sliding unit along a predetermined direction when the fingerprint identifier does not match the expected fingerprint identifier;

wherein the sliding unit is determined by a height of a row having a highest frequency of occurrence in the target experimental data, and a gap of the row having the highest frequency of occurrence in the target experimental data.

2. The method of claim 1, wherein the step of determining a fingerprint identifier of a data segment corresponding to the target experimental data selected by the data segmentation window of a predetermined size further comprises:
determining a byte size of the data segment corresponding to the target experimental data in the data segmentation window;
generating the fingerprint identifier according to the data segment when the byte size is within a predetermined range;
moving the data segmentation window by a sliding unit along a predetermined direction when the byte size is not within the predetermined range.

3. The method of claim 1, wherein the step of determining an expected fingerprint identifier from a predetermined expected fingerprint identifier sequential table according to the position of the data segment further comprises:
determining a partitioning number of the current data block according to the position of the data segment;
determining the expected fingerprint identifier from the expected fingerprint identifier sequential table according to the partitioning number.

4. The method of claim 1, wherein the step of generating a data block index table according to the data blocks further comprises:
determining a hash value, a pattern string and a bit-address corresponding to each of the data blocks;
generating the data block index table according to the data block identifier, the hash value, the pattern string and the bit-address.

5. The method of claim 4, wherein the step of selecting the target matching mode from the plurality of predetermined matching modes according to the data block index table further comprises:
determining a mapping between the pattern string and the data block according to the data block index table;
selecting a shortest time-consuming matching mode as the target matching mode from the predetermined matching modes according to the mapping.

6. An apparatus for automatically collecting and matching laboratory data, wherein the apparatus comprises:
a memory;
a processor; and
one or more computer programs stored in the memory and executable on the processor, wherein the one or more computer programs comprise:
instructions for obtaining a creation time of experimental data input from at least one testing equipment, and determining target experimental data corresponding to a target time in accordance with the creation time;
instructions for segmenting the target experimental data into a plurality of data blocks;
instructions for generating a data block index table according to the data blocks, wherein the data block index table comprises at least one data block identifier;
instructions for selecting a target matching mode from a plurality of predetermined matching modes according to the data block index table;
instructions for obtaining the data block identifier upon determining the target experimental data in a storage node is loaded, and extracting data content in the target experimental data corresponding to the data block identifier by the target matching mode;

wherein the one or more computer programs further comprise:
instructions for obtaining a granularity parameter of the target experimental data;
instructions for generating a target hash value corresponding to the target experimental data according to the granularity parameter; and
instructions for storing the target hash value in a target storage node upon determining the target hash value is different from a hash value stored in the target storage node;

wherein the instructions for segmenting further comprises:
  instructions for determining a fingerprint identifier of a data segment corresponding to the target experimental data selected by a data segmentation window of a predetermined size;
  instructions for determining a data segmentation point of the target experimental data according to a position of a data segment and the fingerprint identifier; and
  instructions for segmenting the target experimental data into corresponding data blocks in accordance with the data segmentation point;
wherein the instructions for determining a data segmentation point of the target experimental data according to a position of a data segment and the fingerprint identifier further comprises:
  instructions for determining an expected fingerprint identifier from a predetermined expected fingerprint identifier sequential table according to the position of the data segment;
  instructions for configuring a lower boundary of the current data segmentation window as the data segmentation point when the fingerprint identifier matches the expected fingerprint identifier; and
  instructions for moving the data segmentation window by one sliding unit along a predetermined direction when the fingerprint identifier does not match the expected fingerprint identifier;
wherein the sliding unit is determined by a height of a row having a highest frequency of occurrence in the target experimental data and a go of the row having the highest frequency of occurrence in the target experimental data.

7. The apparatus of claim 6, wherein the instructions for determining a fingerprint identifier of a data segment corresponding to the target experimental data selected by the data segmentation window of a predetermined size further comprises:
  instructions for determining a byte size of the data segment corresponding to the target experimental data in the data segmentation window;
  instructions for generating the fingerprint identifier according to the data segment when the byte size is within a predetermined range;
  instructions for moving the data segmentation window by a sliding unit along a predetermined direction when the byte size is not within the predetermined range.

8. The apparatus of claim 6, wherein the instructions for determining an expected fingerprint identifier from a predetermined expected fingerprint identifier sequential table according to the position of the data segment further comprises:
  instructions for determining a partitioning number of the current data block according to the position of the data segment;
  instructions for determining the expected fingerprint identifier from the expected fingerprint identifier sequential table according to the partitioning number.

9. The apparatus of claim 6, wherein the instructions for generating a data block index table according to the data blocks further comprises:
  instructions for determining a hash value, a pattern string and a bit-address corresponding to each of the data blocks;
  instructions for generating the data block index table according to the data block identifier, the hash value, the pattern string and the bit-address.

10. The apparatus of claim 9, wherein the instructions for selecting the target matching mode from the plurality of predetermined matching modes according to the data block index table further comprises:
  instructions for determining a mapping between the pattern string and the data block according to the data block index table;
instructions for selecting a shortest time-consuming matching mode as the target matching mode from the predetermined matching modes according to the mapping.

* * * * *